(12) United States Patent
Wybo

(10) Patent No.: US 9,622,684 B2
(45) Date of Patent: Apr. 18, 2017

(54) NEURAL LOCATING SYSTEM

(71) Applicant: Innovative Surgical Solutions, LLC, Southfield, MI (US)

(72) Inventor: Christopher Wybo, Highland, MI (US)

(73) Assignee: Innovative Surgical Solutions, LLC, Wixom, MI (US)

( * ) Notice: Subject to any disclaimer, the term of this patent is extended or adjusted under 35 U.S.C. 154(b) by 438 days.

(21) Appl. No.: 14/032,924

(22) Filed: Sep. 20, 2013

(65) Prior Publication Data
US 2015/0088029 A1    Mar. 26, 2015

(51) Int. Cl.
*A61B 5/11* (2006.01)
*A61B 5/00* (2006.01)

(52) U.S. Cl.
CPC .......... *A61B 5/1107* (2013.01); *A61B 5/1104* (2013.01); *A61B 5/4029* (2013.01); *A61B 5/4893* (2013.01); *A61B 5/0093* (2013.01); *A61B 5/6844* (2013.01); *A61B 5/746* (2013.01); *A61B 2505/05* (2013.01)

(58) Field of Classification Search
CPC ..... A61B 5/1107; A61B 5/107; A61B 5/1072; A61B 5/6844; A61B 5/6886; A61B 5/0093; A61B 7/00; A61B 7/006
USPC ............................ 600/554, 586, 587; 607/48
See application file for complete search history.

(56) References Cited

U.S. PATENT DOCUMENTS 3,200,814 A    8/1965 Taylor et al.
3,565,080 A    2/1971 Ide et al.
3,797,010 A    3/1974 Adler et al.
(Continued)

FOREIGN PATENT DOCUMENTS

EP    1575010 A1    9/2005
FR    2920087 A1    2/2009
(Continued)

OTHER PUBLICATIONS

Anderson et al. (2010). An analysis of agreement between MMG vs. EMG systems for identification of nerve location during spinal procedures. Spine Journal, 10(9), 93S-94S. doi:http://dx.doi.org/10.1016/j.spinee.2010.07.249.*
(Continued)

*Primary Examiner* — David J McCrosky
(74) *Attorney, Agent, or Firm* — Quinn IP Law

(57) ABSTRACT

A neural monitoring system includes an elongate medical instrument, a non-invasive mechanical sensor, and a processor. The elongate medical instrument has a distal end portion configured to extend within an intracorporeal treatment area of a subject, and a plurality of electrodes disposed on the distal end portion. Each electrode is respectively configured to provide an electrical stimulus. The non-invasive mechanical sensor is configured to be placed in mechanical communication with a muscle of the subject and to generate a mechanomyography output signal corresponding to a sensed mechanical movement of the muscle. The processor is provided in communication with the elongate medical instrument and the mechanical sensor, and is configured to receive the mechanomyography output signal, and determine a relative direction between a nerve and the distal end portion of the elongate medical instrument using the received mechanomyography output signal.

16 Claims, 10 Drawing Sheets

(56) References Cited

U.S. PATENT DOCUMENTS

| | | | |
|---|---|---|---|
| 4,817,628 | A | 4/1989 | Zealear et al. |
| 5,284,153 | A | 2/1994 | Raymond et al. |
| 5,284,154 | A | 2/1994 | Raymond et al. |
| 5,775,331 | A | 7/1998 | Raymond et al. |
| 6,324,432 | B1 | 11/2001 | Rigaux et al. |
| 6,361,508 | B1 | 3/2002 | Johnson et al. |
| 6,466,817 | B1 | 10/2002 | Kaula et al. |
| 6,500,128 | B2 | 12/2002 | Marino |
| 6,564,078 | B1 | 5/2003 | Marino et al. |
| 6,760,616 | B2 | 7/2004 | Hoey et al. |
| 6,807,438 | B1 | 10/2004 | Brun Del Re et al. |
| 6,972,199 | B2 | 12/2005 | Lebouitz et al. |
| 7,050,848 | B2 | 5/2006 | Hoey et al. |
| 7,079,883 | B2 | 7/2006 | Marino et al. |
| 7,177,677 | B2 | 2/2007 | Kaula et al. |
| 7,207,949 | B2 | 4/2007 | Miles et al. |
| 7,216,001 | B2 | 5/2007 | Hacker et al. |
| 7,236,832 | B2 | 6/2007 | Hemmerling et al. |
| 7,470,236 | B1* | 12/2008 | Kelleher ............ A61B 5/04001 600/554 |
| 7,522,953 | B2 | 4/2009 | Kaula et al. |
| 7,578,819 | B2 | 8/2009 | Bleich et al. |
| 7,582,058 | B1 | 9/2009 | Miles et al. |
| 7,657,308 | B2 | 2/2010 | Miles et al. |
| 7,664,544 | B2 | 2/2010 | Miles et al. |
| 7,668,588 | B2 | 2/2010 | Kovacs |
| 7,691,057 | B2 | 4/2010 | Miles et al. |
| 7,892,173 | B2 | 2/2011 | Miles et al. |
| 7,905,840 | B2 | 3/2011 | Pimenta et al. |
| 7,942,826 | B1 | 5/2011 | Scholl et al. |
| 7,959,577 | B2 | 6/2011 | Schmitz et al. |
| 7,962,191 | B2 | 6/2011 | Marino et al. |
| 7,981,058 | B2 | 7/2011 | Akay |
| 7,991,463 | B2 | 8/2011 | Kelleher et al. |
| 8,000,782 | B2 | 8/2011 | Gharib et al. |
| 8,016,776 | B2 | 9/2011 | Bourget et al. |
| 8,027,716 | B2 | 9/2011 | Gharib et al. |
| 8,055,349 | B2* | 11/2011 | Gharib ................. A61B 5/0488 600/554 |
| 8,068,912 | B2 | 11/2011 | Kaula et al. |
| 8,075,499 | B2 | 12/2011 | Nathan et al. |
| 8,090,436 | B2 | 1/2012 | Hoey et al. |
| 8,133,173 | B2 | 3/2012 | Miles et al. |
| 8,137,284 | B2 | 3/2012 | Miles et al. |
| 8,147,421 | B2* | 4/2012 | Farquhar ............. A61B 5/0488 600/546 |
| 8,165,653 | B2 | 4/2012 | Marino et al. |
| 8,343,065 | B2 | 1/2013 | Bartol et al. |
| 8,343,079 | B2 | 1/2013 | Bartol et al. |
| 8,517,954 | B2 | 8/2013 | Bartol et al. |
| 2001/0031916 | A1 | 10/2001 | Bennett et al. |
| 2002/0038092 | A1 | 3/2002 | Stanaland et al. |
| 2002/0165590 | A1 | 11/2002 | Crowe et al. |
| 2003/0074037 | A1 | 4/2003 | Moore et al. |
| 2004/0077969 | A1 | 4/2004 | Onda et al. |
| 2004/0082877 | A1* | 4/2004 | Kouou et al. ................. 600/546 |
| 2004/0186535 | A1 | 9/2004 | Knowlton |
| 2004/0230138 | A1 | 11/2004 | Inoue et al. |
| 2004/0243018 | A1 | 12/2004 | Organ et al. |
| 2005/0075578 | A1 | 4/2005 | Gharib et al. |
| 2005/0085741 | A1 | 4/2005 | Hoskonen et al. |
| 2005/0102007 | A1 | 5/2005 | Ayal et al. |
| 2005/0240086 | A1 | 10/2005 | Akay |
| 2005/0245839 | A1 | 11/2005 | Stivoric et al. |
| 2005/0280531 | A1 | 12/2005 | Fadem et al. |
| 2005/0283204 | A1 | 12/2005 | Buhlmann et al. |
| 2006/0020177 | A1 | 1/2006 | Seo et al. |
| 2006/0052726 | A1 | 3/2006 | Weisz et al. |
| 2006/0135888 | A1 | 6/2006 | Mimnagh-Kelleher et al. |
| 2006/0270949 | A1 | 11/2006 | Mathie et al. |
| 2007/0038155 | A1 | 2/2007 | Kelly, Jr. et al. |
| 2007/0049826 | A1* | 3/2007 | Willis ............................ 600/439 |
| 2007/0265675 | A1 | 11/2007 | Lund et al. |
| 2007/0276270 | A1 | 11/2007 | Tran |
| 2008/0051643 | A1 | 2/2008 | Park et al. |
| 2008/0058656 | A1 | 3/2008 | Costello et al. |
| 2008/0167695 | A1 | 7/2008 | Tehrani et al. |
| 2008/0234767 | A1 | 9/2008 | Salmon et al. |
| 2008/0287761 | A1 | 11/2008 | Hayter et al. |
| 2008/0306363 | A1 | 12/2008 | Chaiken et al. |
| 2008/0306397 | A1 | 12/2008 | Bonmassar et al. |
| 2008/0312560 | A1 | 12/2008 | Jamsen et al. |
| 2008/0312709 | A1 | 12/2008 | Volpe et al. |
| 2009/0036747 | A1 | 2/2009 | Hayter et al. |
| 2009/0062696 | A1 | 3/2009 | Nathan et al. |
| 2009/0069709 | A1 | 3/2009 | Schmitz et al. |
| 2009/0069722 | A1 | 3/2009 | Flaction et al. |
| 2009/0076336 | A1 | 3/2009 | Mazar et al. |
| 2009/0171381 | A1 | 7/2009 | Schmitz et al. |
| 2009/0192416 | A1 | 7/2009 | Ernst et al. |
| 2009/0228068 | A1 | 9/2009 | Buhlmann et al. |
| 2009/0247910 | A1 | 10/2009 | Klapper |
| 2009/0306741 | A1 | 12/2009 | Hogle et al. |
| 2009/0318779 | A1 | 12/2009 | Tran |
| 2010/0137748 | A1 | 6/2010 | Sone et al. |
| 2010/0152619 | A1 | 6/2010 | Kalpaxis et al. |
| 2010/0152622 | A1 | 6/2010 | Teulings |
| 2010/0152623 | A1 | 6/2010 | Williams |
| 2010/0168559 | A1 | 7/2010 | Tegg et al. |
| 2010/0262042 | A1* | 10/2010 | Kirn ............................. 600/586 |
| 2010/0292617 | A1 | 11/2010 | Lei et al. |
| 2011/0004207 | A1 | 1/2011 | Wallace et al. |
| 2011/0230782 | A1* | 9/2011 | Bartol .................. A61B 5/6843 600/546 |
| 2011/0237974 | A1 | 9/2011 | Bartol et al. |
| 2011/0301665 | A1* | 12/2011 | Mercanzini .......... A61B 5/6868 607/45 |
| 2012/0053491 | A1 | 3/2012 | Nathan et al. |
| 2012/0191003 | A1* | 7/2012 | Garabedian et al. ......... 600/554 |
| 2013/0123659 | A1 | 5/2013 | Bartol et al. |
| 2013/0253533 | A1 | 9/2013 | Bartol et al. |
| 2014/0066803 | A1* | 3/2014 | Choi ............................ 600/554 |
| 2015/0032022 | A1* | 1/2015 | Stone et al. .................. 600/547 |

FOREIGN PATENT DOCUMENTS

| | | |
|---|---|---|
| WO | 0078209 A2 | 12/2000 |
| WO | 2007024147 A1 | 3/2007 |

OTHER PUBLICATIONS

Bartol, S., & Wybo, C. (2010). The use of mechanomyography (MMG) to locate nerves during spine surgery procedures. Spine Journal, 10(9), 128S. doi:http://dx.doi.org/10.1016/j.spinee.2010.07.333.*

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

(56) References Cited

OTHER PUBLICATIONS

Murphy, Chris; Campbell, Niall; Caulfield, Brian; Ward, Tomas and Deegan, Catherine; "Micro Electro Mechanical Systems Based Sensor for Mechanomyography", 19th international conference Biosignal 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

\* cited by examiner

NEURAL LOCATING SYSTEM

TECHNICAL FIELD

The present invention relates generally to a surgical diagnostic system for detecting the presence of one or more nerves.

BACKGROUND

Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

SUMMARY

A neural monitoring system includes an elongate medical instrument, a non-invasive mechanical sensor, and a processor. The elongate medical instrument has a distal end portion configured to extend within an intracorporeal treatment area of a subject, and a plurality of electrodes disposed on the distal end portion. Each electrode is respectively configured to provide an electrical stimulus.

The non-invasive mechanical sensor is configured to be placed in mechanical communication with a muscle of the subject and to generate a mechanomyography output signal corresponding to a sensed mechanical movement of the muscle.

The processor is provided in communication with the elongate medical instrument and the mechanical sensor. It may be configured to receive the mechanomyography output signal, and to determine a relative direction between a nerve that innervates the muscle and the distal end portion of the elongate medical instrument via the received mechanomyography output signal.

In one configuration, the processor is further configured to provide a respective electrical stimulus to each of the plurality of electrodes, wherein the electrical stimulus has a predetermined current magnitude. The processor may then monitor an amplitude of the received mechanomyography signal, and determine a respective distance between each of the plurality of electrodes and a nerve using the current magnitude of the electrical stimulus and the amplitude of the received mechanomyography signal. From these determined distances, the processor may determine the relative direction between the nerve and the distal end portion of the elongate medical instrument, for example, through triangulation. This direction may be provided to a user, for example, via a display to aid the user in avoiding actions that may jeopardize the integrity of the identified nerve.

In one configuration, the plurality of electrodes may include at least four electrodes, where three are aligned on a plane that is transverse to a longitudinal axis of the medical instrument. In such an embodiment, a fourth electrode may be disposed on a distal side of the plane and separated from the plane by a distance.

The above features and advantages and other features and advantages of the present invention are readily apparent from the following detailed description of the best modes for carrying out the invention when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
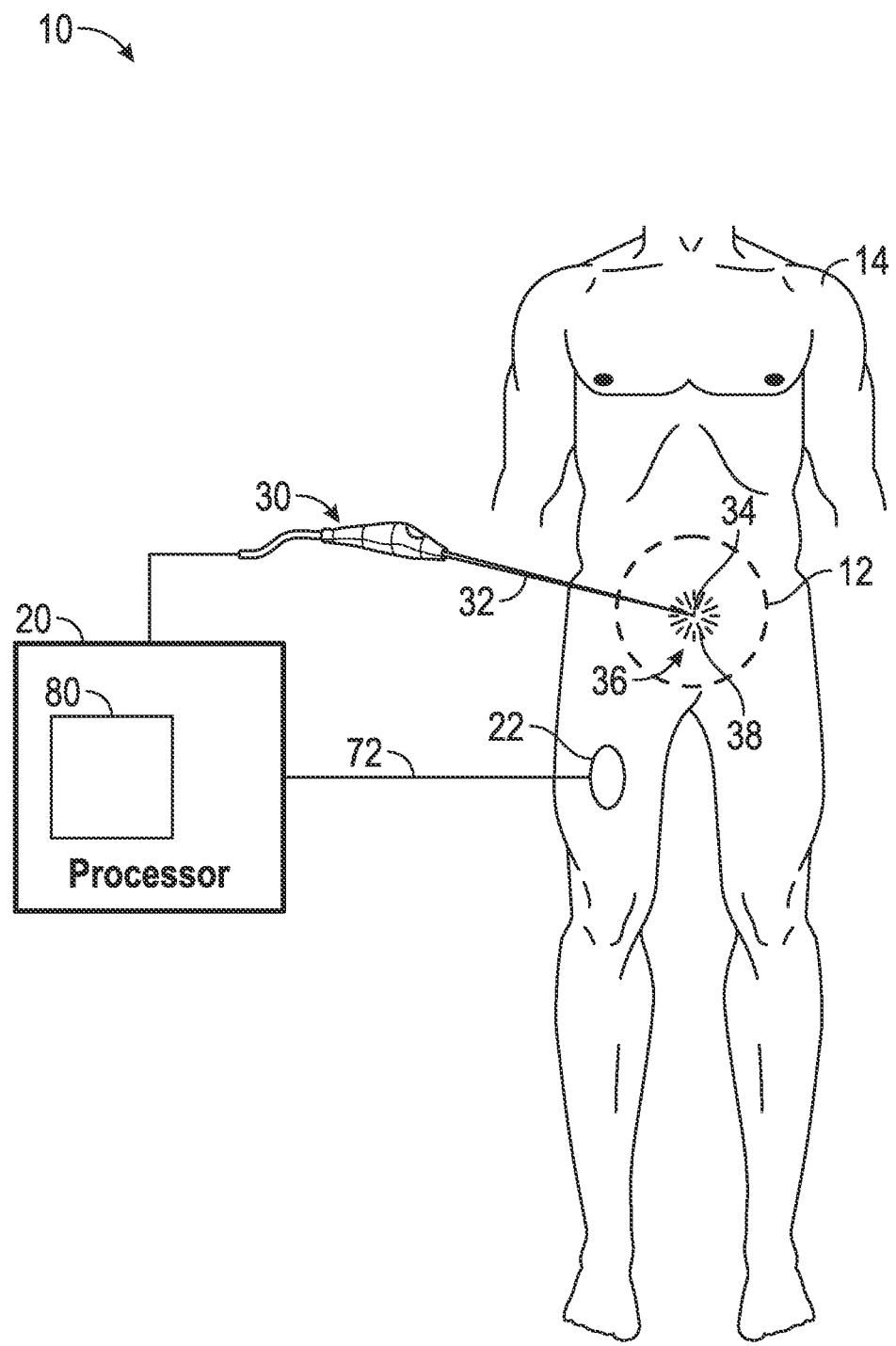
FIG. 1 is a schematic diagram of a neural monitoring system for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14. As will be described in greater detail below, the system 10 may monitor one or more muscles of the subject 14 for a mechanical motion, and may be capable of discriminating an artificially-induced mechanical response of a muscle (also referred to as an "artificially-induced mechanical muscle response") from a subject-intended muscle contraction/relaxation and/or an environmentally caused movement. If an artificially-induced mechanical muscle response is detected during the procedure, the system 10 may provide an indication to a user, such as via a display or perform another appropriate action.

As used herein, an artificially-induced mechanical muscle response refers to a contraction or relaxation of a muscle in response to a stimulus that is not received through natural sensory means (e.g., sight, sound, taste, smell, and touch). Instead, it is a contraction/relaxation of a muscle that is induced by the application of a stimulus directly to a nerve that innervates the muscle. Examples of stimuli that may cause an "artificially-induced" muscle response may include an electrical current applied directly to the nerve or to intracorporeal tissue or fluid immediately surrounding the nerve. In this example, if the applied electrical current is sufficiently strong and/or sufficiently close to the nerve, it may artificially cause the nerve to depolarize (resulting in a corresponding contraction of the muscle innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially-induced mechanical muscle response, a muscle innervated by the artificially depolarized nerve may physically contract or relax (i.e., a mechanical response). Such a mechanical reaction may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state, and is distinguished from other global translations of the muscle.

The neural monitoring system 10 may include a processor 20 that is in communication with at least one mechanical sensor 22. The mechanical sensor 22 may include, for example, a strain gauge, a force transducer, a position encoder, an accelerometer, a piezoelectric material, or any other transducer or combination of transducers that may convert a physical motion into a variable electrical signal.

Each mechanical sensor 22 may specially be configured to monitor a local mechanical movement of a muscle of the subject 14. For example, each sensor 22 may include a fastening means, such as an adhesive material/patch, that allows the sensor 22 to be adhered, bandaged, or otherwise affixed to the skin of the subject 14 (i.e. affixed on an external skin surface). Other examples of suitable fastening means may include bandages, sleeves, or other elastic fastening devices that may hold the sensor 22 in physical contact with the subject 14. Alternatively, the mechanical sensor 22 (and/or coupled device) may be configured to monitor a local mechanical movement of a muscle by virtue of its physical design. For example, the sensors/coupled devices may include catheters, balloons, bite guards, orifice plugs or endotracheal tubes that may be positioned within a lumen or natural opening of the subject to monitor a response of the lumen or orifice, or of a muscle that is directly adjacent to and/or connected with the lumen or orifice. In one configuration, the mechanical sensor may be a non-invasive device, whereby the term "non-invasive" is intended to mean that the sensor is not surgically placed within the body of the subject (i.e., via cutting of tissue to effectuate the placement). For the purposes of this disclosure, non-invasive sensors may include sensors that are placed within naturally occurring body lumens that are accessible without the need for an incision.

In one configuration, the sensor 22 may include a contact detection device, that may provide an indication if the sensor 22 is in physical contact with the skin of the subject 14. The contact detection device may, for example, include a pair of electrodes that are configured to contact the skin of the subject 14 when the sensor 22 is properly positioned. The sensor 22/contact detection device may then monitor an impedance between the electrodes to determine whether the electrodes are in contact with the skin. Other examples of suitable contact detection devices may include capacitive touch sensors or buttons that protrude slightly beyond the surface of the sensor.

The system 10 may further include one or more elongate medical instruments 30 that are capable of selectively providing a stimulus within the intracorporeal treatment area 12 of the subject 14 (i.e., also referred to as a stimulator 30). For example, in one configuration, the elongate medical instrument 30 may include a probe 32 (e.g., a ball-tip probe, k-wire, or needle) that has one or more electrodes 34 disposed on a distal end portion 36. The electrode(s) 34 may be selectively electrified, at either the request of a user/physician, or at the command of the processor 20, to provide an electrical stimulus 38 to intracorporeal tissue of the subject. In other configurations, the elongate medical instrument 30 may include a dialator, retractor, clip, cautery probe, pedicle screw, or any other medical instrument that may be used in an invasive medical procedure. Regardless of the instrument, if the intended artificial stimulus is an electrical current, the instrument 30 may include one or more selectively electrifiable electrodes 34 disposed at a portion of the instrument that is intended to contact tissue within the intracorporeal treatment area 12 during a procedure.

During a surgical procedure, the user/surgeon may selectively administer the stimulus to intracorporeal tissue within the treatment area 12 to identify the presence of one or more nerve bundles or fibers. For an electrical stimulus 38, the user/surgeon may administer the stimulus, for example, upon depressing a button or foot pedal that is in communication with the system 10, and more specifically in communication with the stimulator 30. The electrical stimulus 38 may, for example, be a discrete pulse (e.g., a step pulse) having a pulse width within the range of about 30 µs to about 500 µs. In other examples, the discrete pulse may have a pulse width within the range of about 50 µs to about 200 µs, or within the range of about 75 µs to about 125 µs. The discrete pulse may be periodically applied at a frequency of, for example, between about 1 Hz and about 10 Hz.

Figure 2:
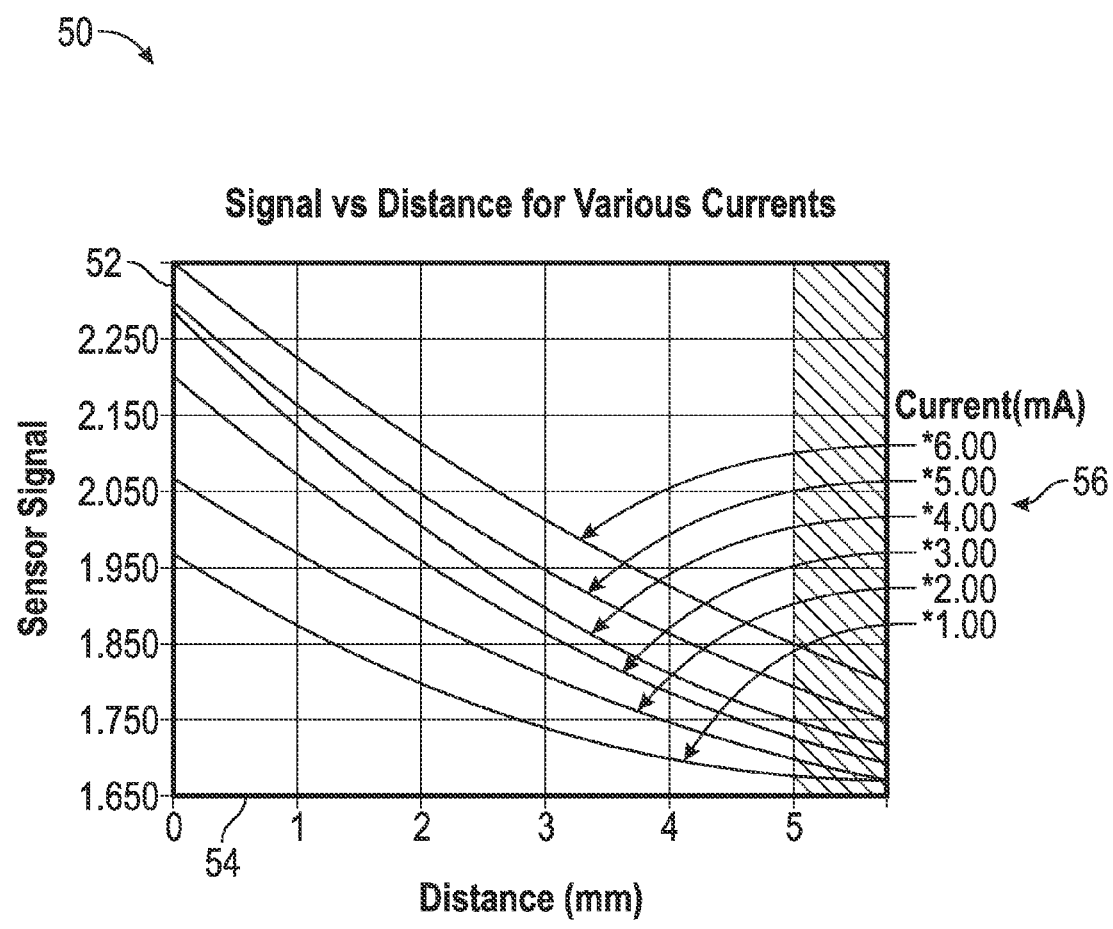
FIG. 2 is a schematic graph of the relationship between MMG output signal amplitude, stimulator electrical current, and distance between a stimulator electrode and a nerve.

If a nerve extends within a predetermined distance of the electrode 34, the electrical stimulus 38 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, and the magnitude of the stimulus current. FIG. 2 illustrates a graph 50 of these relationships where the magnitude 52 of the sensed response is shown as a function of the distance 54 between the stimulator and the nerve, and the magnitude 56 of the applied electrical current stimulus. In one configuration, the relationships illustrated in FIG. 2 (or variants thereof) may be stored in a lookup table associated with the processor 20. The lookup table may then be employed by the processor 20 to provide an approximate distance 54 between the electrode 34 and the nerve, given a known stimulus magnitude 56 and a measured mechanical muscle response magnitude 52.

Referring again to FIG. 1, prior to beginning a surgical procedure, the one or more mechanical sensors 22 may be placed in mechanical communication with one or more muscles of the subject 14. In the present context, a sensor 22 may be in mechanical communication with the muscle if it can physically detect a movement, velocity, acceleration, strain or other physical response of the muscle, either via direct contact with the muscle, or via a mechanical relationship through one or more intermediate materials and/or tissues (e.g., skin and/or subcutaneous tissue).

Figure 3:
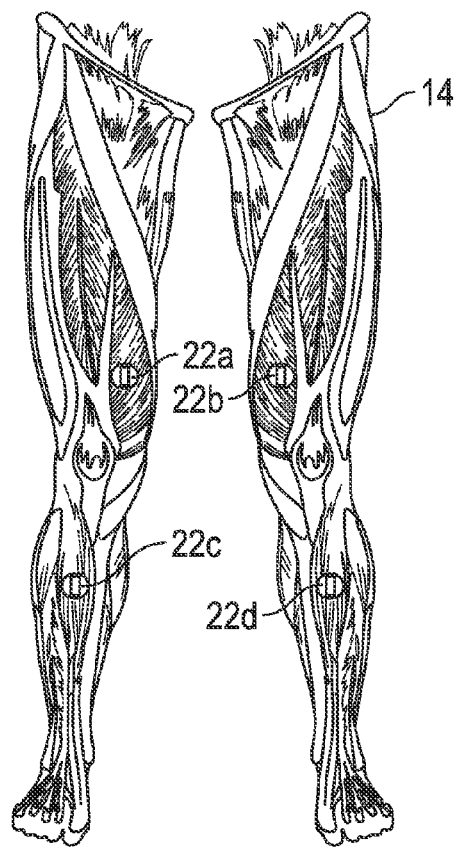
FIG. 3 is a schematic front view of the placement of a plurality of mechanical sensors on the legs of a subject.
Figure 4:
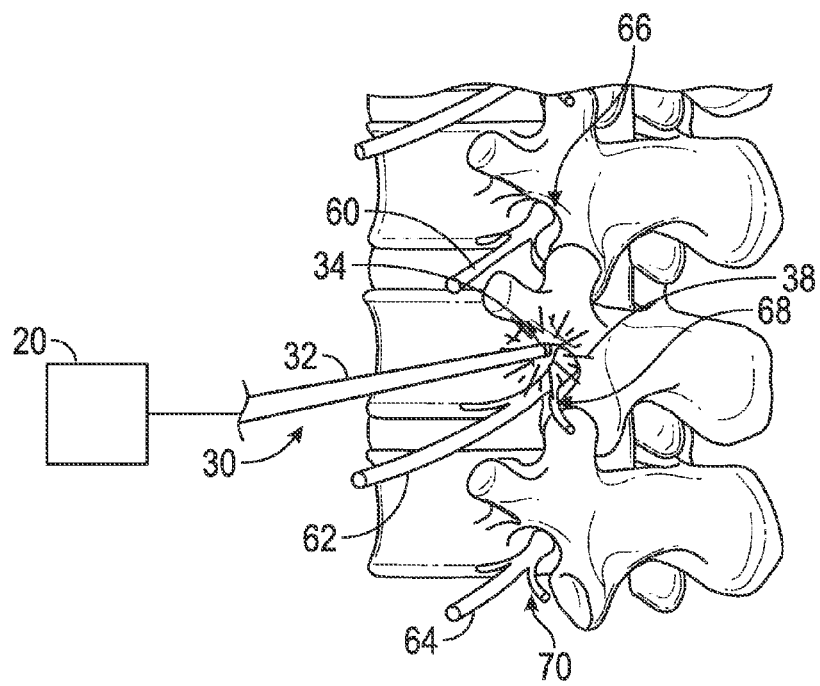
FIG. 4 is a schematic side view of an intracorporeal treatment area including a portion of the lumbar spine.

FIG. 3 illustrates an example of the placement of a plurality of mechanical sensors 22 for a surgical procedure that may occur proximate the L2, L3, and/or L4 vertebrae of the lumbar spine (shown schematically in FIG. 4). The nerves 60, 62 and 64 exiting the L2, L3 and L4 foramen 66, 68, 70 may therefore either lie within the treatment area 12 (i.e., the area surrounding the L2, L3, and/or L4 vertebrae), or may be immediately proximate to this area. Using common anatomical knowledge, the surgeon may understand that damage to these nerves 60, 62, 64 may affect the functioning of the vastus medialis muscles and the tibialis anterior muscles. As such, the surgeon may place mechanical sensors 22a-22d on or near the vastus medialis muscles and the tibialis anterior muscles to guard against inadvertent manipulation of the nerves during the procedure. For example, mechanical sensors 22a and 22b are placed on the vastus medialis muscles, which are innervated by the nerves 60, 62 exiting the L2 and L3 foramen 66, 68, and sensors 22c and 22d are placed on the tibialis anterior muscles, which are innervated by the nerves 64 exiting the L4 foramen 70.

In general, each mechanical sensor 22 may generate a mechanomyography (MMG) output signal (schematically shown in FIG. 1 at 72) that corresponds to a sensed mechanical movement/response of the adjacent muscle. The MMG output signal 72 may be either a digital or analog signal, and may typically be provided to the processor 20 through either wired or wireless communication means (e.g., through a physical wire, or using radio frequency communication protocols, such as according to IEEE 802.11 or another protocol such as Bluetooth). As a specific signal, the MMG output signal 72 is intended to be separate and distinct from any electrical potentials of the muscle or skin (often referred to as electromyography (EMG) signals). While electrical (EMG) and mechanical (MMG) muscle responses may be related, their relationship is complex, and not easily described (e.g., electrical potentials are very location specific, with a potentially variable electrical potential across the volume of the muscle of interest).

Referring again to FIG. 1, the processor 20 may be in communication with the stimulator 30 and the mechanical sensor 22, and may be configured to receive the MMG output signal 72 from the mechanical sensor 22. The processor 20 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

The processor 20 may be configured to automatically perform one or more signal processing algorithms 80 or methods to determine whether a sensed mechanical movement (i.e., via the MMG output signal 72) is representative of an artificially-induced mechanical muscle response or if it is merely a subject-intended muscle movement and/or an environmentally caused movement. These processing algorithms 80 may be embodied as software or firmware, and may either be stored locally on the processor 20, or may be readily assessable by the processor 20.

During an invasive procedure, as discussed above, the processor 20 may determine the distance between an electrically stimulating electrode 34 and a nerve by providing an electrical stimulus 38 to the electrode 34 at a known or measurable current magnitude, and by measuring the magnitude of the mechanical muscle response. In one configuration, a surgeon may be able to surmise the relative location of the nerve by dithering the stimulator 30, and monitoring the changes in the magnitude of the response (i.e., moving the stimulator 30 closer to the nerve would yield a greater response). In another embodiment, the system 10 may be configured to automatically determine the position of the nerve relative to the stimulator 30 without the need for mechanical dithering. In this embodiment, the stimulator 30 may be provided with a plurality of electrodes that may collectively be used to triangulate the position of the nerve.

FIGS. 5A-5B and 6A-6B illustrate two embodiments 90, 92 of the distal end portion 36 of a multi-electrode stimulator 94 that may be used to determine a position of a nerve relative to the stimulator 94. In each embodiment 90, 92, the distal end portion 36 of the stimulator 94 includes a plurality of electrodes 96 disposed in a spaced relationship. Each electrode may be selectively energized at the direction of a processor 20 and may be configured to provide an electrical stimulus 38 to tissue of the subject.

Figure 5A:
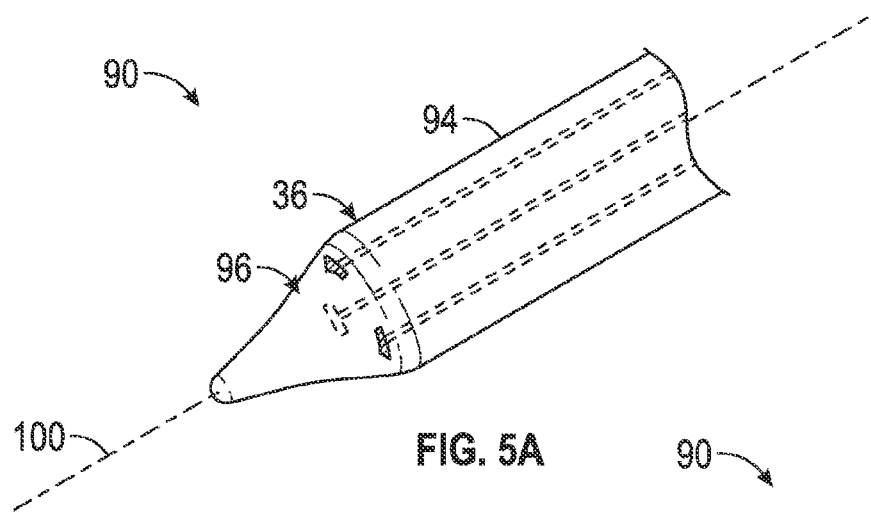
FIG. 5A is a schematic isometric view of a first embodiment of a multi-electrode stimulator.
Figure 5B:
FIG. 5B is a schematic bottom view of the multi-electrode stimulator shown in FIG. 5A.

FIGS. 5A and 5B generally illustrate an embodiment 90 of a multi-electrode stimulator 94 that includes three electrodes 98a, 98b, 98c disposed in a spaced arrangement. The stimulator 94 includes a longitudinal axis 100 that extends between a proximal end portion and the distal end portion 36. In one configuration, the three electrodes 98a, 98b, 98c may be disposed on the stimulator 94 such that they define a plane that is that is transverse to the longitudinal axis 100.

Figure 6A:
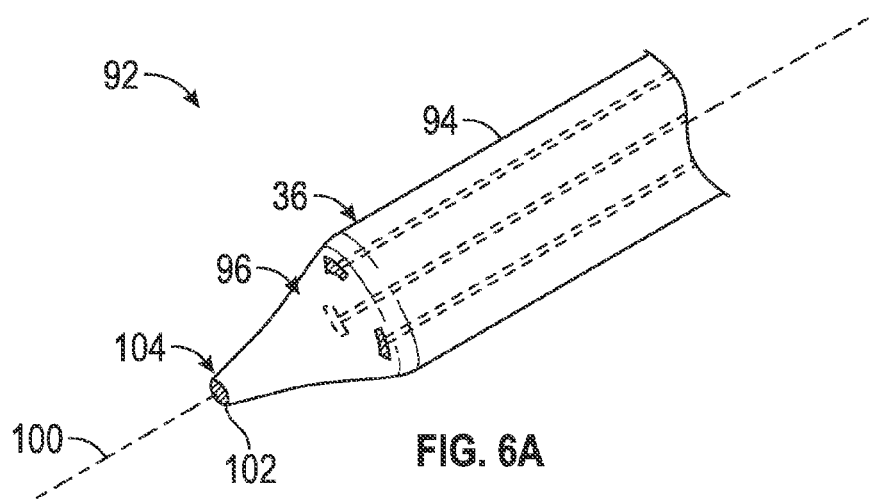
FIG. 6A is a schematic isometric view of a second embodiment of a multi-electrode stimulator.
Figure 6B:
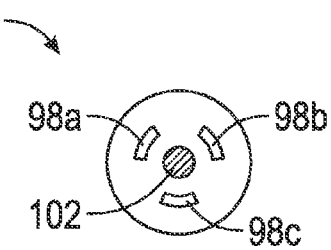
FIG. 6B is a schematic bottom view of the multi-electrode stimulator shown in FIG. 6A.

FIGS. 6A and 6B illustrate an embodiment 92 of a stimulator 94 that is similar to the embodiment 90 provided in FIGS. 5A and 5B, though further includes a fourth electrode 102 disposed on a tip portion 104 of the stimulator 94.

In both designs, the electrodes 98a, 98b, 98c (and 102) are configured to make leading contact with intracorporeal tissue as the probe is being advanced in a longitudinal direction. This maximizes the likelihood that each electrode will remain in contact with the tissue. Examples of designs that place the electrodes on a leading surface include, for example, positioning an electrode on a tip of the probe (such as with the fourth electrode 102), positioning an electrode on a sloped or conical advancing face (such as electrodes 98a, 98b, 98c), and/or extending/protruding the electrode radially outward from a perimeter surface.

As mentioned above, the spaced array of electrodes may allow the system 10 to triangulate the location of the nerve relative to the stimulator. In general, the system 10 may resolve (n−1) degrees of freedom for an array of (n) electrodes. For example, a stimulator 30 with 2 electrodes may determine the position of a nerve along a single axis, a stimulator 30 with 3 electrodes may determine the position of a nerve within a plane, and a stimulator 30 with 4 electrodes may determine the position of a nerve within three dimensional space.

Figure 7:
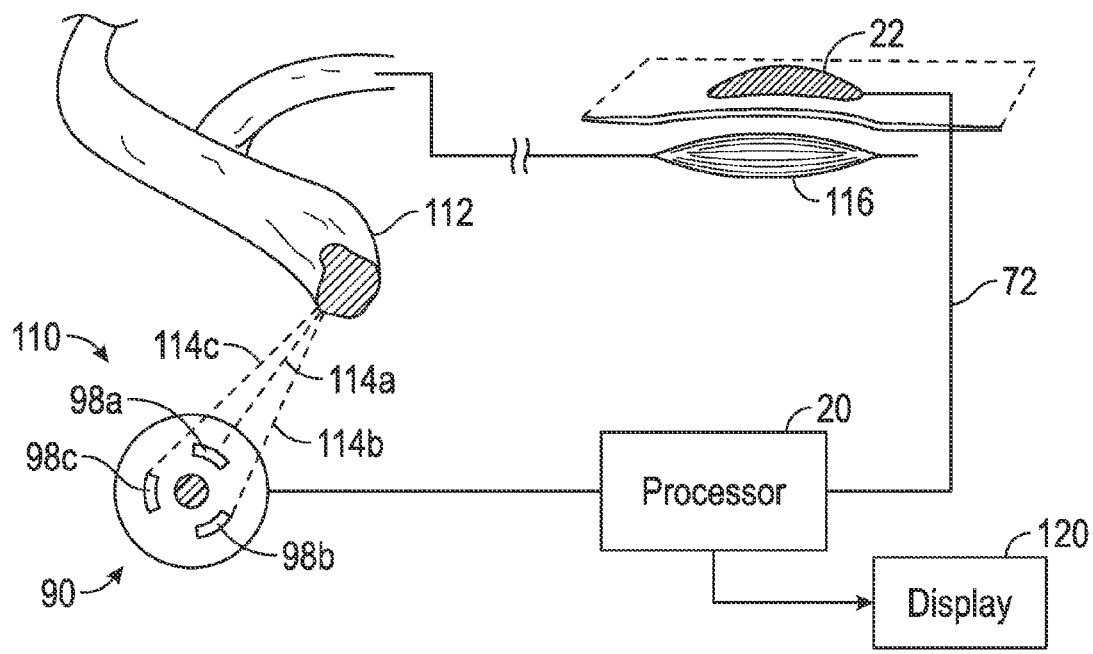
FIG. 7 is a schematic diagram of a neural monitoring system, including a multi-electrode stimulator, being used to triangulate the position of a nerve relative to the stimulator.

FIG. 7 schematically illustrates a cross-sectional view 110 of the stimulator 90 being used to triangulate the position of a nerve 112 relative to the stimulator 90. As shown, each electrode 98a, 98b, 98c may emit a respective electrical stimulus 114a, 114b, 114c that may be received by the nerve 112. The stimuli 114a, 114b, 114c may be provided either sequentially, or concurrently (e.g., via frequency multiplexing). The processor 20 may then monitor a mechanical sensor 22 that is in mechanical communication with a muscle 116 innervated by the nerve 112 for a response to each of the respective stimuli 114a, 114b, 114c. Using the monitored muscle response, and the known magnitude of the respective stimuli, the processor may determine a respective distance between each electrode 98a, 98b, 98c and the nerve 112. The processor 20 may then use these determined distances to triangulate the position of the nerve 112 relative to the stimulator 90 within an approximate statistical margin of error. This determined relative position may include either simply a vector heading, or may include both a vector heading and a distance.

Figure 8:
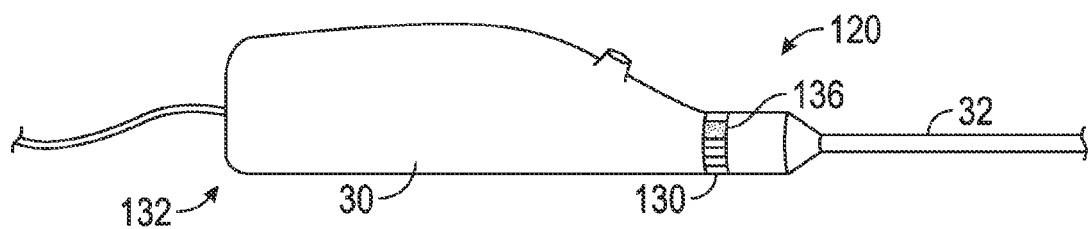
FIG. 8 is a schematic side view of an embodiment of a multi-electrode stimulator.
Figure 9:
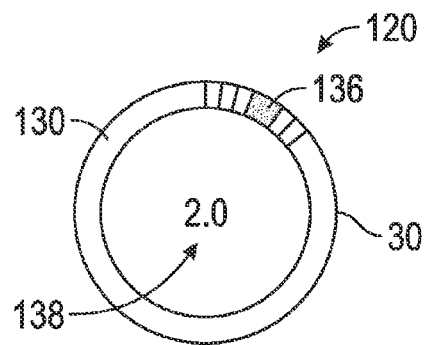
FIG. 9 is a schematic end view of the proximal end portion of an embodiment of a multi-electrode stimulator.
Figure 10:
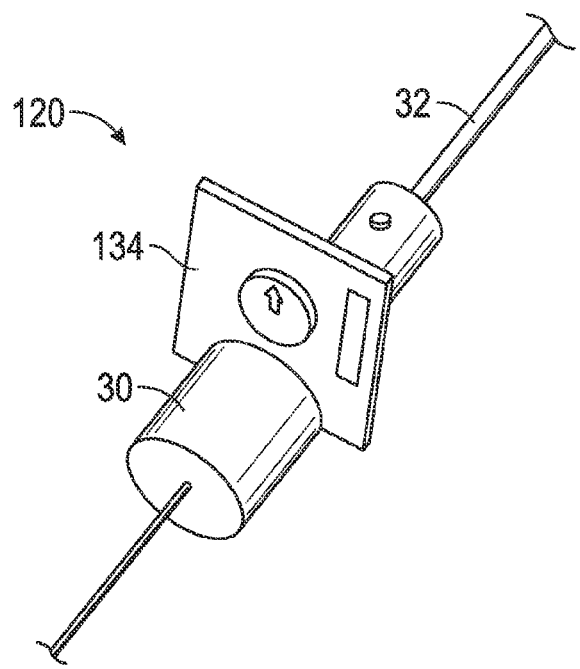
FIG. 10 is a schematic isometric view of an embodiment of a multi-electrode stimulator.

Once the heading direction and/or distance is determined, the processor 20 may provide an indication of the determined relative position of the nerve to a user, such as via a display device 120. FIGS. 8, 9, and 10 illustrate three embodiments of a display device 120 that may be used to provide a user with an indication of directionality. In FIG. 8, the display device 120 resembles an annular light ring 130 that is disposed about an outer perimeter of the stimulator 30, adjacent to the probe 32. FIG. 9 illustrates a similar light ring 130 that may be disposed on a proximal end 132 of the stimulator 30. Finally, FIG. 10 illustrates a digtal display device 134 that may be associated with the stimulator 30, incorporated as a standalone display, or integrated into a multi-purpose monitor. In each case, the display device 120 may provide a visual indicator 136 of the detected position of the nerve relative to the stimulator 30.

With reference to FIGS. 8 and 9, in one configuration, the visual indicator 136 may include a light bar that may rotate around the annular light ring 130 to indicate directionality. The intensity, color, and/or circumferential width of the light bar 136 may be used to indicate the statistical confidence of the determined directionality, the position of the nerve along the longitudinal axis (i.e., wider may signify that the nerve lies further beyond the distal tip), and/or may be used to indicate the distance between the stimulator 30 and the nerve (i.e., a wider bar may indicate a closer proximity). Additionally, a digital indicator 138 may be also included to indicate proximity.

The digital display device 134 provided in FIG. 10 may be, for example an LCD display that may be incorporated with and/or hinged to the stimulator 30, or may be a standalone device. The digital display device 134 may include similar indicators as described above with respect to the annular light right 130, and may be adapted to display an indication of a vector heading and/or a proximity/distance.

Figure 11:
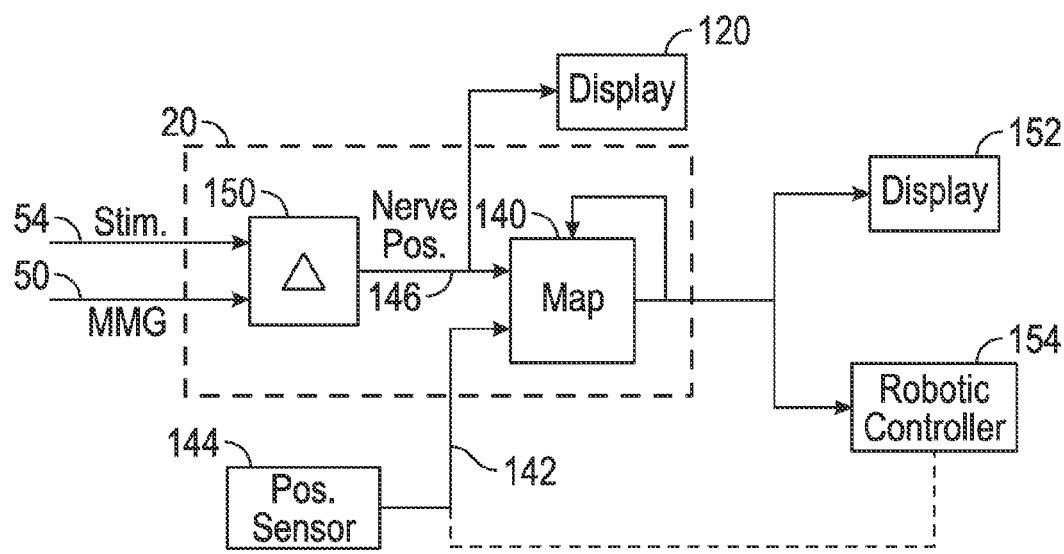
FIG. 11 is a schematic diagram of an embodiment of a nerve mapping processor.

While the above-described technology is useful in providing a real-time directional reference to a user, in a further extension, the processor 20 may be configured to maintain a three-dimensional nerve map 140, such as shown in FIG. 11. In this embodiment, the processor 20 may receive a position signal 142 from a locating device 144 that may register the stimulator 30 in three-dimensional space. The processor may use this position signal 142 together with the determined relative nerve position information 146 from a triangulation module 150 to progressively construct and/or refine a nerve intensity map. As the distal end portion of the stimulator 30 is moved within the intracorporeal space, the map may be refined using newly determined triangulation information that may be registered within a global coordinate frame.

Figure 12:
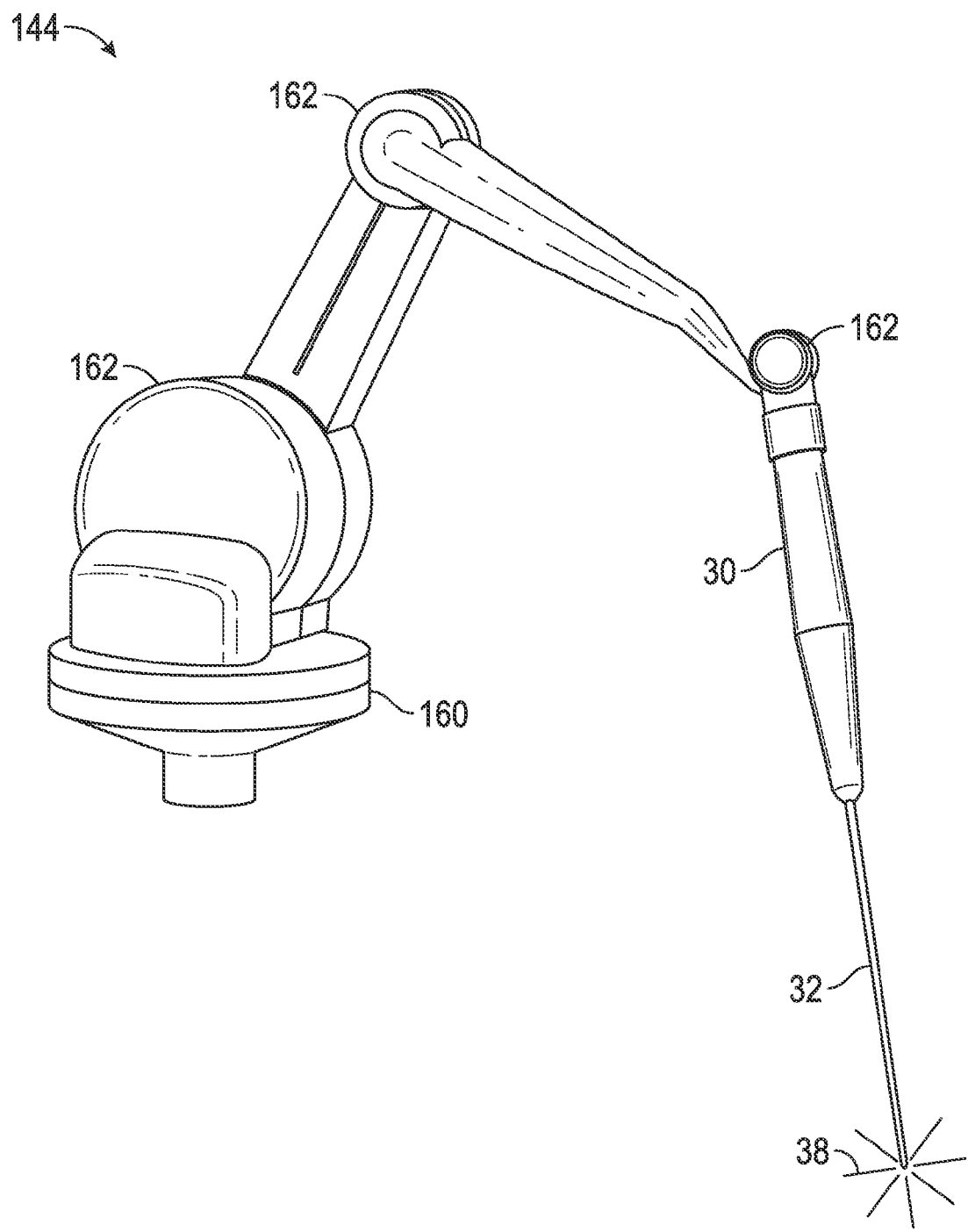
FIG. 12 is a schematic side view of a locating device that may register a stimulator in three-dimensional space.

In one embodiment, the locating device 144 may include a multi-axial, spatial input device 160 that may be affixed to the stimulator 30, and may monitor the position of the stimulator throughout the procedure. An embodiment of a spatial input device 160 is generally shown in FIG. 12. In this design, the spatial input device may include a plurality of instrumented rotatable joints 162, which may monitor the physical location of the stimulator 30 in three spatial dimensions (x, y, and z), as well as in three orientations (roll, pitch, and yaw). In this manner, the position of the distal end portion may be reconciled and provided to the processor 20. Commercially available examples of a spatial input device of this nature include the Touch Haptic Input Device or the Phantom Haptic Input Device, both made by Geomagic Solutions.

In another embodiment, the distal end portion of the stimulator 30 may be located within three-dimensional space using a non-contact position locating device. Examples of non-contact position locating devices may use ultrasound, electrical fields, magnetic fields, fluoroscopy, or optical recognition to locate the stimulator (i.e., the distal end portion of the stimulator) within three-dimensional space.

Once the three dimensional nerve map 140 is created, it may be output to a display device 152 (which may be similar or the same as display device 120), where it may be dynamically viewed during a procedure, or may be merged with other imagery such as fluoroscopy or endoscopy. Alternatively the nerve map 140 may be output to a robotic controller 154 where it may be used to dynamically control/constrain the motion of a robotically controlled end effector.

Figure 13:
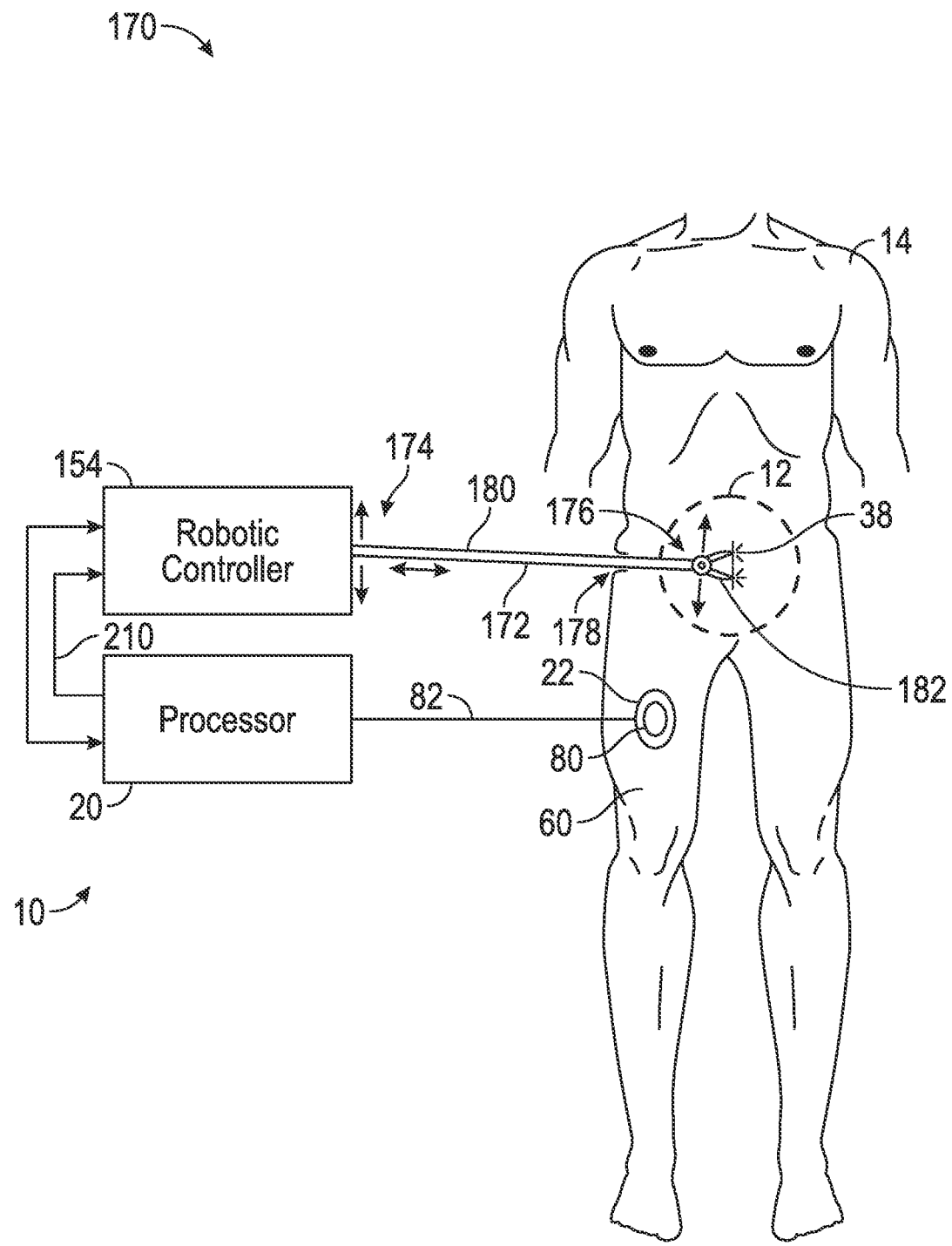
FIG. 13 is a schematic diagram of a robotically controlled surgical system for including a neural monitoring system for detecting the position of a surgical tool relative to a nerve.

FIG. 13 schematically illustrates an embodiment of a robotic surgical system 170 that may employ the present nerve detection/mapping techniques. Such a system is further described in U.S. patent application Ser. No. 13/428,693, filed 23 Mar. 2012, entitled "ROBOTIC SURGICAL SYSTEM WITH MECHANOMYOGRAPHY FEEDBACK," which is incorporated by reference in its entirety and for all of the disclosure set forth therein.

As illustrated, the displayed embodiment of the robotic surgical system 170 includes a nerve detection processor 20 and a robotic controller 154. The robotic controller 154 is configured to control the motion of an elongate surgical instrument 172 that includes a proximal end portion 174 and a distal end portion 176.

During a surgical procedure, the surgical instrument 172 may extend through an opening 178 in the body of the subject 14, with the distal end portion 176 disposed within the intracorporeal treatment area 12, and the proximal end portion 174 disposed outside of the subject 14. In one configuration, the surgical instrument 172 may generally be defined by a rigid elongate body 180, such that movement of the proximal end portion 174 of the instrument 172 may result in a predictable movement of the distal end portion 176.

The surgical instrument 172 may further include an end effector 182 disposed at the distal end portion 176. The end effector 182 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 182 may be configured to selectively rotate and/or articulate about the distal end portion 176 of the surgical instrument 172 to enable a greater range of motion/dexterity during a procedure. The end effector 182 and/or distal end portion 176 of the instrument 172 may include a plurality of electrodes (as generally discussed above with respect to FIGS. 5A, 5B, 6A, and 6B), that may each be configured to provide a respective electrical stimulus 184 to tissue within the treatment area 12.

In one embodiment, such as generally illustrated in FIG. 13, the end effector 182 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 180 of the instrument 172.

Figure 14:
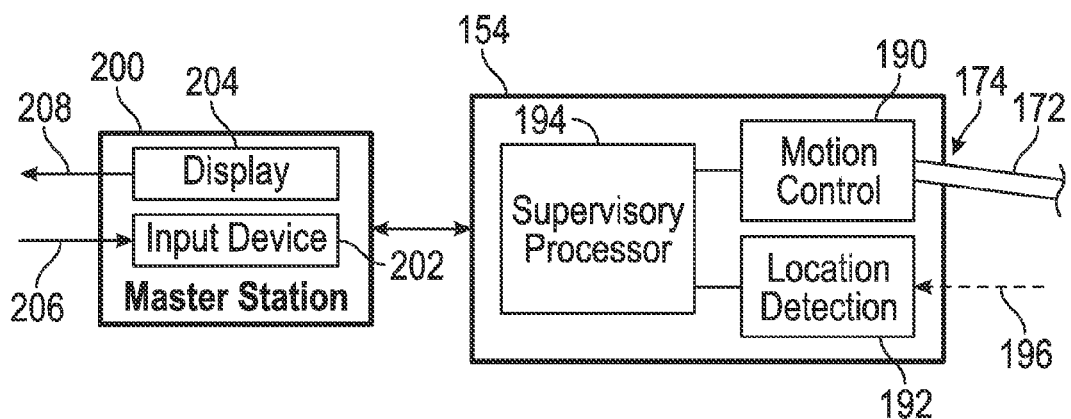
FIG. 14 is a schematic diagram of a robotic controller.

The robotic controller 154 may be responsible for controllably performing a minimally invasive surgical procedure within the body of the subject 14 by controllably manipulating the proximal end 174 of the surgical instrument 172 in a manner that results in a controlled motion of the distal end portion 176. As generally illustrated in FIG. 14, in one configuration, the robotic controller 154 may include a motion controller 190, a location detection module 192 and a supervisory processor 194. The motion controller 190 may include a plurality of motors, linear actuators, or other such components that may be required to manipulate the proximal end 174 of the surgical instrument 172 in six or more degrees of freedom. (e.g., three degrees of translation, three degrees of rotation, and/or one or more degrees of actuation). Additionally, the motion controller 190 may include one or more processors or digital computers and/or power electronics that may be required to convert a received motion command into a physical actuation of a motor or actuator.

The location detection module 192 may include one or more digital computers or processing devices that may be configured to determine the position/motion of the distal end portion 176 of the surgical instrument 172, such as relative to one or more external reference frames. In one configuration, the location detection module 192 may monitor the behavior of the motion controller 190 to determine the motion of the distal end portion 176 using kinematic relationships of the surgical instrument 172. In another configuration, the location detection module 192 may receive a location signal 196 from an external, locating device 144, which may resolve the position of the distal end portion 176 of the surgical instrument 172 using, for example, encoded joints/linkages, ultrasound energy, magnetic energy, or electromagnetic energy that may be propagated through the subject 14.

The supervisory processor 194 may be embodied as one or more digital computers or data processing devices, each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 44 or readily accessible thereby may be stored in ROM or other suitable tangible memory location and/or memory device, and automatically executed by associated hardware components of the processor 194 to provide the respective control functionality. In one embodiment, the supervisory processor 194 may provide the motion controller 190 with actuation commands in a closed loop manner using the positional feedback provided by the location detection module 192. The supervisory processor 194 may perform any combination of feedforward, feedback, and/or predictive control schemes to accurately control the motion and/or actuation of the distal end portion 16 of the surgical instrument 12.

Additionally, the robotic controller 154 may be in communication with a master station 200 that includes a user input device 202 and a user feedback device such as a display 204 (e.g., which may be similar to display 154 provided in FIG. 11). The user input device 202 may receive an input 206 from a user that corresponds to an intended movement of the distal end portion 176 of the surgical instrument 172. The master station 200 may then provide a motion command to the robotic controller 154 that corresponds to the received input 206. Similarly, the master station 200 may receive visual information 208 from the robotic controller and convey it to the user via the display 204.

While FIG. 14 provides one embodiment of a robotic controller 154, other embodiments, configurations, and or control schemes may similarly be used to manipulate the surgical instrument 172 in a manner that results in a controlled and intended motion of the distal end portion 176. While the robotic controller 154 and surgical instrument 12 described above are generally of the kind used for robotic laparoscopy, such description is made for illustrative purposes and should not be limiting. Other minimally invasive surgical systems that employ a robotic controller 154 to control the motion of the distal end of an elongate surgical instrument may include, for example, robotic catheter systems and/or robotic endoscopic systems.

Referring again to FIG. 13, the robotic surgical system 170 includes (and/or may be in communication with) a neural monitoring system 10 that may digitally communicate with the robotic controller 154. As described above, the neural monitoring system 10 may include at least one mechanical sensor 22 and a nerve monitoring processor 20 in communication with the mechanical sensor 22. The neural monitoring system 10 may provide the robotic controller 154 with an awareness of nerves that may be adjacent to the distal end portion 176 of the surgical instrument 172. In this manner, the robotic system 170 may avoid manipulating tissue (either through translational motion or actuation of an end effector 182) that may jeopardize neural integrity.

If the nerve monitoring processor 20 detects the presence of a nerve proximate to the elongate instrument 172 (i.e., via the mechanical sensor 22), it may then provide a control signal 210 to the robotic controller 154. The control signal 210 may include an indication of the relative position/direction of the nerve, and may further include an indication of proximity between the distal end portion 176 of the surgical instrument 172 and the nerve.

Upon receipt of a control signal 210, the robotic controller 154 may artificially constrain the motion of the distal end portion 176 of the surgical instrument 172 to avoid inadvertent contact with a proximate nerve. For example, in one configuration, the robotic controller 154 may be configured to prevent all motion of the distal end portion 176 of the surgical instrument 172 in response to the received control signal 210. As such, if the distal end portion 176 was in motion, the received control signal 210 may cause the controller 154 to halt such motion and await a further command from the user. Additionally, the robotic controller 154 may be configured to limit or prevent actuation of an end effector 182 upon receipt of the control signal 210. Conversely, in certain therapeutic procedures, the robotic controller 154 may be configured to actuate the end effector 182 upon receipt of the control signal 210 (e.g., selectively deliver ablative energy to tissue proximate to the nerve).

Figure 15:
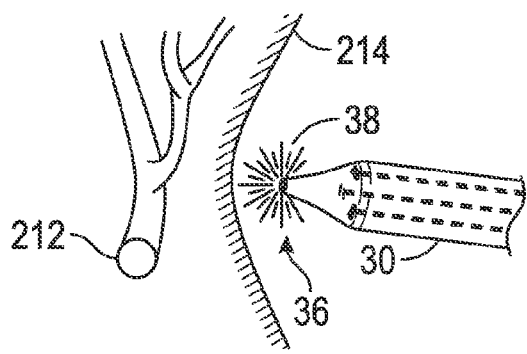
FIG. 15 is a schematic cross-sectional view of a distal end portion of an elongate surgical instrument moving with respect to a nerve of a subject.
Figure 16:
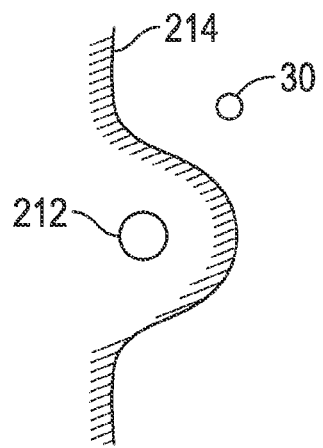
FIG. 16 is a schematic cross-sectional view of FIG. 15, with a virtual barrier being erected about the nerve.

In another configuration, such as schematically illustrated in FIG. 15, upon receipt of the control signal 210, the robotic controller may limit the instrument's ability to move in a direction toward the nerve 212. In still another configuration, the robotic controller 154 may construct a virtual barrier 214 about the nerve 212 which may prevent the instrument 172 from moving within a prescribed distance of the nerve 212. The virtual barrier 214 may be maintained in an associated memory of the robotic controller 154 and/or may be associated with the 3d nerve map 140 that may be maintained by the nerve monitoring processor 20. In general, the virtual barrier 214 may limit the allowed range of motion of the surgical instrument 172, such that the surgical instrument 172 is artificially restricted from crossing the virtual barrier 214. As generally illustrated in FIG. 16, as the surgical instrument 172 moves and acquires additional nerve directionality information, the virtual barrier 214 may be refined.

In still another configuration, once a nerve is detected, the robotic controller 154 may be configured to vary the permitted speed of the distal end portion 176 of the surgical instrument 172 as a function of the indicated proximity between the real-time location of the instrument 172 and the estimated relative position of the nerve. As such, the instrument 172 may be allowed to move more quickly and/or at a higher rate of speed when it is farther from the nerve. In this manner, the precision of the movements may be enhanced as one or more nerves become more proximate.

If the presence of a proximate nerve is detected, and/or if an action is performed by the robotic controller 154 to adjust or limit the allowed motion of the surgical instrument 172, the robotic controller 154 may likewise transmit an alert (i.e., a visual alert or an auditory alert) to the user via the master station 200.

While the above-described technology is primarily focused on determining the position of a nerve relative to a stimulator 30, the nerve monitoring processor 20 may further include one or more filtering algorithms that may allow the system 10 to distinguish an artificially-induced mechanical muscle response from a patient-intended response and/or a global translation of a portion of the patient. Suitable filtering algorithms may include analog filtering algorithms, such as those described in U.S. Pat. No. 8,343,079, which is incorporated by reference in its entirety, and/or digital filtering algorithms, such as those described in U.S. patent application Ser. No. 13/965,457, filed on 13 Aug. 2013 and entitled "Neural Event Detection," which is incorporated by reference in its entirety. These filtering algorithms may look at time correlations between an applied stimulus and a detected response, the rise time/slope of a monitored response, and/or frequency characteristics of the monitored response to discern whether a detected mechanical muscle movement is attributable to a provided stimulus. In one configuration, such filtering may precede any proximity detection and/or position triangulation.

Figure 17:
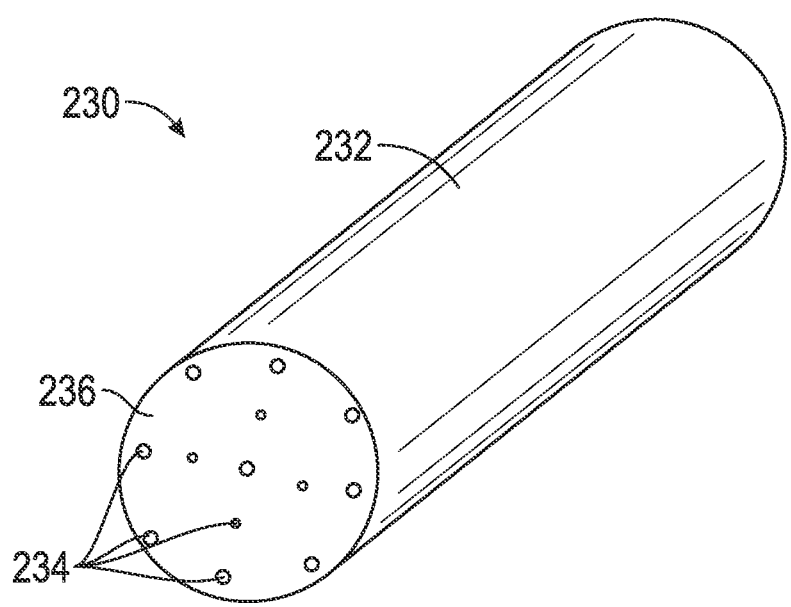
FIG. 17 is a schematic isometric view of a distal end portion of a third embodiment of a multi-electrode stimulator.
Figure 18:
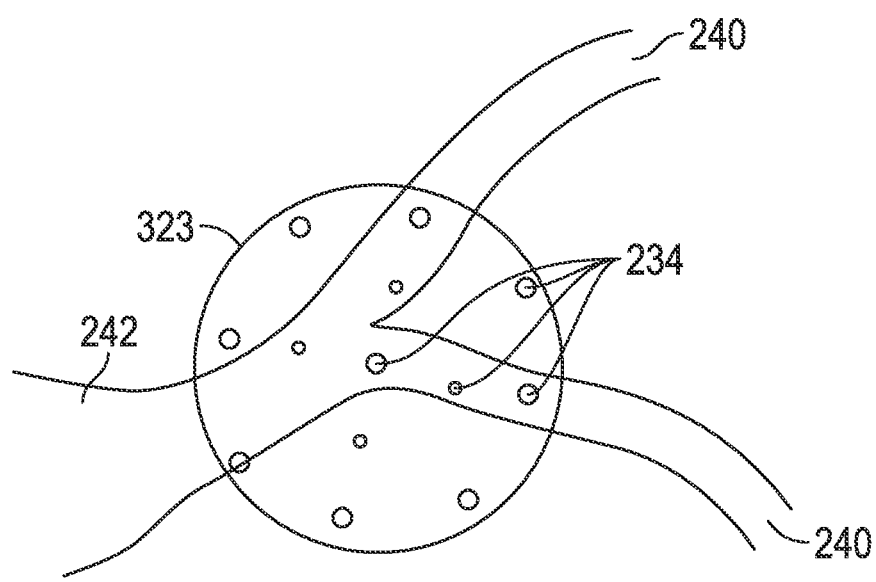
FIG. 18 is a schematic top view of the electrodes of the stimulator provided in FIG. 17 disposed relative to a branched nerve.

While FIGS. 5A, 5B, 6A, 6B illustrate two embodiments of a potential stimulator design, other designs may similarly be possible. For example, as shown in FIG. 17, in one embodiment, the stimulator 230 may have a generally cylindrical body 232, and may include a plurality of electrodes 234 disposed on a distal end face 236. As generally illustrated in FIG. 18, which is viewed along the longitudinal axis of the stimulator 230 in a distal-facing direction, such a stimulator 230 may be useful in determining the location of a plurality of nerve branches 240 that extend from a common trunk 242. In this instance, by including eight or more electrodes 234, the stimulator 230 may be used to resolve nerve position with greater resolution than a stimulator with only three or four electrodes. In one configuration, such a stimulator 230 may be configured to slide within the inner diameter of an annular surgical dilator, and may be used to determine if any nerves extend across the annular opening.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:
1. A neural monitoring system comprising:
an elongate medical instrument having a distal end portion configured to extend within an intracorporeal treatment area of a subject, the elongate medical instrument including a plurality of electrodes disposed on the distal end portion, each electrode respectively being configured to provide an electrical stimulus;
a non-invasive mechanical sensor configured to be placed in mechanical communication with a muscle of the subject and to generate a mechanomyography output signal corresponding to a sensed mechanical movement of the muscle; and
a processor in communication with the elongate medical instrument and the mechanical sensor, and configured to:
provide a respective electrical stimulus to each of the plurality of electrodes, the electrical stimulus having a predetermined current magnitude;
receive the mechanomyography output signal; and
triangulate a relative direction between a nerve and the distal end portion of the elongate medical instrument via an amplitude of the received mechanomyography output signal and a current magnitude of each respective electrical stimulus, wherein the nerve innervates the muscle.
2. The system of claim 1, wherein the processor is configured to provide the respective electrical stimulus to each of the plurality of electrodes in a sequential manner.

3. The system of claim 1, wherein the processor is configured to provide the respective electrical stimulus to each of the plurality of electrodes in a concurrent manner;
   wherein each respective electrical stimulus includes a plurality of current pulses provided at a stimulation frequency; and
   wherein the stimulation frequency for each respective electrical stimulus is unique.

4. The system of claim 1, wherein the non-invasive mechanical sensor includes an accelerometer, a microphone, a strain gauge, or a piezoelectric device.

5. The system of claim 1, further comprising a display device; and
   wherein the processor is further configured to provide an indication of the relative direction between the nerve and the distal end portion of the elongate medical instrument via the display device.

6. The system of claim 1, wherein the processor is further configured to maintain a three dimensional nerve map using the triangulated relative direction between the nerve and the distal end portion of the elongate medical instrument and a monitored location of the distal end portion of the elongate medical instrument within the intracorporeal treatment area.

7. The system of claim 6, further comprising a display device; and
   wherein the processor is further configured to display the three dimensional nerve map via the display device.

8. The system of claim 6, further comprising a display device; and
   wherein the processor is further configured to merge the three dimensional nerve map with an anatomical image, and display the merged three dimensional nerve map and anatomical image via the display device.

9. The system of claim 6, further comprising a robotic controller operative to control the motion of the elongate medical instrument; and
   wherein processor is further configured to output the three dimensional nerve map to the robotic controller; and
   wherein the robotic controller is configured to at least one of control or constrain the motion of the elongate medical instrument in response to the received three dimensional nerve map.

10. A neural monitoring system comprising:
   an elongate medical instrument having a distal end portion configured to extend within an intracorporeal treatment area of a subject, the elongate medical instrument including at least four electrodes disposed on the distal end portion, each electrode respectively being configured to provide an electrical stimulus;
   a non-invasive mechanical sensor configured to be placed in mechanical communication with a muscle of the subject and to generate a mechanomyography output signal corresponding to a sensed mechanical movement of the muscle; and
   a processor in communication with the elongate medical instrument and the mechanical sensor, and configured to:
      provide a respective electrical stimulus to each of the at least four electrodes, the electrical stimulus having a predetermined current magnitude;
      receive the mechanomyography output signal; and
      triangulate a relative direction between a nerve and the distal end portion of the elongate medical instrument via an amplitude of the received mechanomyography output signal and a current magnitude of each respective electrical stimulus, wherein the nerve innervates the muscle.

11. The system of claim 10, wherein the elongate medical instrument has a longitudinal axis extending between a proximal end portion and the distal end portion of the instrument; and
   wherein three of the at least four electrodes define a plane that is transverse to the longitudinal axis.

12. The system of claim 11, wherein one of the at least four electrodes is disposed on a distal side of the plane and is separated from the plane by a distance.

13. The system of claim 10, wherein the processor is configured to provide the respective electrical stimulus to each of the at least four electrodes in a sequential manner.

14. The system of claim 10, wherein the processor is configured to provide the respective electrical stimulus to each of the at least four electrodes in a concurrent manner;
   wherein each respective electrical stimulus includes a plurality of current pulses provided at a stimulation frequency; and
   wherein the stimulation frequency for each respective electrical stimulus is unique.

15. The system of claim 10, wherein the non-invasive mechanical sensor includes an accelerometer, a microphone, a strain gauge, or a piezoelectric device.

16. The system of claim 10, wherein the at least four electrodes is at least 8 electrodes disposed in a common plane.

* * * * *